(12) United States Patent
You et al.

(10) Patent No.: US 9,120,951 B2
(45) Date of Patent: Sep. 1, 2015

(54) OPHTHALMIC LENSES, OPHTHALMIC LENS COATING COMPOSITIONS, AND METHODS FOR MANUFACTURING OPHTHALMIC LENSES

(75) Inventors: Xiaorong You, Morristown, NJ (US); Phil Johnson, Morristown, NJ (US)

(73) Assignee: Honeywell International Inc., Morristown, NJ (US)

( * ) Notice: Subject to any disclaimer, the term of this patent is extended or adjusted under 35 U.S.C. 154(b) by 106 days.

(21) Appl. No.: 13/818,740

(22) PCT Filed: Aug. 31, 2011

(86) PCT No.: PCT/US2011/049947
§ 371 (c)(1),
(2), (4) Date: Mar. 21, 2013

(87) PCT Pub. No.: WO2012/030945
PCT Pub. Date: Mar. 8, 2012

(65) Prior Publication Data
US 2013/0211517 A1 Aug. 15, 2013

(51) Int. Cl.
*C04B 41/50* (2006.01)
*C09D 183/04* (2006.01)
*B29D 11/00* (2006.01)
*G02B 1/04* (2006.01)
*G02B 27/00* (2006.01)
*A61F 2/16* (2006.01)
*A61K 48/00* (2006.01)

(52) U.S. Cl.
CPC ............... *C09D 183/04* (2013.01); *A61F 2/16* (2013.01); *B29D 11/00865* (2013.01); *G02B 1/043* (2013.01); *G02B 27/0006* (2013.01); *A61K 48/00* (2013.01)

(58) Field of Classification Search
CPC .. C09D 183/04; C09D 175/04; C09D 201/04; G02B 1/043; B29D 11/00865
See application file for complete search history.

(56) References Cited

U.S. PATENT DOCUMENTS

| | | | |
|---|---|---|---|
| 5,622,784 A * | 4/1997 | Okaue et al. | 428/447 |
| 6,140,451 A * | 10/2000 | Asai et al. | 528/34 |
| 6,200,626 B1 | 3/2001 | Grobe, III et al. | |
| 6,861,149 B2 * | 3/2005 | Pellerite et al. | 428/428 |
| 7,863,375 B2 * | 1/2011 | Baghdachi et al. | 524/714 |
| 2002/0192380 A1 * | 12/2002 | Elsbernd et al. | 427/314 |
| 2005/0249942 A1 | 11/2005 | Coggio et al. | |
| 2006/0228560 A1 | 10/2006 | Stewart et al. | |
| 2006/0264650 A1 * | 11/2006 | Arora | 556/485 |
| 2008/0090004 A1 * | 4/2008 | Zhang et al. | 427/180 |
| 2009/0257022 A1 * | 10/2009 | Abe et al. | 351/166 |
| 2009/0311518 A1 | 12/2009 | Valeri | |

OTHER PUBLICATIONS

International Search Report for PCT/US2011/049947 dated Apr. 10, 2012.

* cited by examiner

*Primary Examiner* — Margaret Moore
(74) *Attorney, Agent, or Firm* — Ingrassia Fisher & Lorenz PC

(57) ABSTRACT

Ophthalmic lenses, coatings for ophthalmic lenses, and methods for manufacturing ophthalmic lenses are provided herein. In one exemplary embodiment, an ophthalmic lens comprising a polymeric lens has a first surface and second surface. A coating overlies the first surface. The coating comprises a polysiloxane, a polyurethane, an oligomer derived from a polysiloxane or a polyurethane, a polymer derived from a polysiloxane or a polyurethane, or a combination thereof, and a fluorinated material. The coating exhibits a water contact angle of greater than 90° as measured by a goniometer.

3 Claims, No Drawings

OPHTHALMIC LENSES, OPHTHALMIC LENS COATING COMPOSITIONS, AND METHODS FOR MANUFACTURING OPHTHALMIC LENSES

PRIORITY CLAIMS

This application claims the benefit of U.S. Provisional Application No. 61/379,011, filed Sep. 1, 2010.

TECHNICAL FIELD

The present invention generally relates to ophthalmic lenses, ophthalmic lens coating compositions, and methods for manufacturing ophthalmic lenses, and more particularly relates to ophthalmic lenses with abrasion resistance and hydrophobic properties, ophthalmic lens coating compositions that impart abrasion resistance and hydrophobic properties, and methods for manufacturing such ophthalmic lenses.

BACKGROUND

Polymeric ophthalmic lenses have become increasingly popular recently due to their fine optical properties, dimensional stability, impact resistance, and light weight. Common lens-forming materials include CR-39 (diethyleneglycol bis-allyl carbonate), bisphenol A polycarbonate (PC), and poly (methylmethacrylate) (PMMA). Despite the above noted benefits to polymeric lenses, one serious drawback to polymeric ophthalmic lenses has been their susceptibility to scratching, particularly compared to traditional glass lenses.

Consequently, plastic lens surfaces have required treatment to provide a scratch- and/or abrasion-resistant layer on the lens surface to increase the field durability of the lens and retard the development of haze. Consequently, nearly all polymeric lenses have some type of scratch resistant coating. Further, additional coating layers and steps may be required in connection with the scratch resistant coating. Both front and back coatings can be applied in different ways such as dip coating or spin coating. Multiple coatings may also be necessary to obtain other desirable properties such as a mirror coating, and stain and smudge resistance.

In this regard, much research has been devoted to providing coatings for polymeric lenses to improve their abrasion resistance. In one coating method, coatings are applied sequentially in a multi-step process with a finish hard coat layer. As with many of the other coating processes, conventionally cured hard coat finishes also have several drawbacks. In general, some of the coating materials require that a primer be applied separately. While thermal cured hard coatings provide superior scratch resistance, they also require long cure times and high energy consumption for solvent evaporation. UV hard coatings provide fast cure, huge energy savings and high throughput production. However, the scratch resistance is generally poorer than that with thermal cure hard coatings.

Still further, all of the above noted coatings are susceptible to dirt collection and smudging. The surface can be cleaned by wiping with a surfactant-treated cloth or paper tissue, but the cleaning is temporary and the surface will become smudged in a short period of time, requiring repeated cleaning. Until recently, there are primarily two general methods of providing anti-fouling, anti-fingerprint, and easy cleaning features. One type is a surface treatment in the form of an over coating via a two-step process. The other type is UV curable or UV/thermal curable coating via polyfunctional acrylates. The disadvantage of the two-step surface treatment is that it is expensive and is difficult to use for high volume production, especially, for disposable protective articles. The shortcoming of a UV curable or UV/thermal curable coating via polyfunctional acrylates is that it results in relatively poor abrasion resistance as compared to the superior thermal curable polysiloxane/polyurethane based coating.

Accordingly, it is desirable to provide ophthalmic lenses offering easy cleaning features and that have superior abrasion resistance. In addition, it is desirable to provide ophthalmic lens coating compositions that impart to ophthalmic lenses resistance to dirt collection, smudging, and abrasion, cost effectiveness, long lives and suitableness for high volume production. It is also desirable to provide a method for manufacturing ophthalmic lenses that have abrasion resistance and hydrophobic properties, the method being a one-step application process that thermally cures the overlying coating composition. Furthermore, other desirable features and characteristics of the present invention will become apparent from the subsequent detailed description of the invention and the appended claims, taken in conjunction with the accompanying drawings and this background of the invention.

BRIEF SUMMARY

Ophthalmic lenses, coatings for ophthalmic lenses, and methods for manufacturing ophthalmic lenses are provided herein. In one exemplary embodiment, an ophthalmic lens comprising a polymeric lens has a first surface and second surface. A coating overlies the first surface. The coating comprises a polysiloxane, a polyurethane, an oligomer derived from a polysiloxane or a polyurethane, a polymer derived from a polysiloxane or a polyurethane, or a combination thereof, and a fluorinated material. The coating exhibits a water contact angle of greater than 90° as measured by a goniometer.

In another exemplary embodiment, a coating composition for an ophthalmic polymeric lens is provided. The coating composition comprises a polysiloxane, a polyurethane, an oligomer derived from a polysiloxane or a polyurethane, a polymer derived from a polysiloxane or a polyurethane, or a combination thereof. The coating composition further comprises a solvent and a fluorinated material. A thermally cured coating resulting from the coating composition exhibits a water contact angle of greater than 90° as measured by a goniometer when applied in a single coat on the ophthalmic polymeric lens.

In a further exemplary embodiment, a method for forming an ophthalmic lens is provided. The method comprises providing a polymeric lens and preparing a coating composition. The coating composition comprises a polysiloxane, a polyurethane, an oligomer derived from a polysiloxane or a polyurethane, a polymer derived from a polysiloxane or a polyurethane, or a combination thereof. The coating composition further comprises a solvent and a fluorinated material. The coating composition is applied to the polymeric lens and the solvent is evaporated. The polymeric lens is subjected to a thermal treatment after evaporating the solvent to cure the polysiloxane, the polyurethane, the oligomer derived from a polysiloxane or a polyurethane, the polymer derived from a polysiloxane or a polyurethane, or the combination thereof.

DETAILED DESCRIPTION

The following detailed description is merely exemplary in nature and is not intended to limit the invention or the application and uses of the invention. Furthermore, there is no intention to be bound by any theory presented in the preceding background or the following detailed description.

The various exemplary embodiments contemplated herein are directed to ophthalmic lenses, coatings for ophthalmic lenses, and methods for manufacturing ophthalmic lenses. The coating composition includes a thermally-curable polysiloxane(s) or polyurethane(s), or a combination thereof and fluorinated material incorporated therein. Compared to conventional coating compositions, the coating compositions contemplated herein can be applied in a single application and thermally cured, thus decreasing the cost and time of manufacturing and increasing production. In addition, the thermally-cured coating imparts scratch and abrasion resistance to the polymeric ophthalmic lenses. Further, the fluorinated material causes the thermally-cured coatings to exhibit hydrophobic surface properties without altering the curing properties or the optical or mechanical performance of the polysiloxane and/or polyurethane components. Thus, the resulting ophthalmic lenses are resistant to abrasion, scratching, stains, and markings and can easily be cleaned by wiping with a clean cloth, tissue paper, or the like.

In an exemplary embodiment, the ophthalmic lens contemplated herein comprises a polymeric lens. Examples of polymeric lenses suitable for use include, but are not limited to, allyl diglycol carbonate (CR-39 or ADC), bisphenol A polycarbonate (PC), and poly(methylmethacrylate)(PMMA). The lens can have any size and shape as is suitable for a desired application but generally has a first surface through which light enters and a second surface through which the light departs.

The ophthalmic lens contemplated herein further comprises a thermally-cured coating overlying the first surface and, optionally, the second surface of the polymeric lens. In one embodiment, the coating comprises at least one polysiloxane, at least one polyurethane, at least one oligomer derived from a polysiloxane or a polyurethane, at least one polymer derived from a polysiloxane or a polyurethane, or a combination thereof. Examples of polysiloxanes suitable for use in the coating contemplated herein include, but are not limited to polysiloxanes having amino functional groups, polysiloxanes having epoxy functional groups, linear siloxanes, cyclic siloxanes, and the like. Examples of polyurethanes suitable for use in the coating contemplated herein are based on polyisocyanates that include, but are not limited to, Witcobond® W-290H and Witcobond® A-100 available from Chemtura Corporation of Philadelphia, Pa., Bayhydur® 302, Bayhydur® XP-7165, and Desmodur® DA-L available from Bayer Material Science of Germany, and Easaqua XD 401 and Easaqua XM 501 available from Perstorp Group of Sweden. These polysiloxanes and polyurethanes are thermally curable and, thus, provide abrasion resistance superior to oligomers and polymers that are ultravioletly curable.

In an exemplary embodiment, the coating further comprises a fluorinated material. The fluorinated material is incorporated into the coating to impart hydrophobic surface properties without altering the curing properties or the optical or mechanical performance of the polysiloxane and/or polyurethane component. As discussed in more detail below, the coating, as fabricated, is solvent-based. Accordingly, in one embodiment, to facilitate compatibility between the polar fluorinated material and the solvent-based polysiloxane and/or polyurethane component, the fluorinated material comprises a fluorinated surfactant. Fluorinated surfactants also improve the compatibility between polar solvents, to be discussed below, and the polysiloxane and/or polyurethane. Examples of fluorinated surfactants suitable for use in the coatings contemplated herein include, but are not limited to, PolyFox® PF-636, PF-656, PF-6320 and PF-6520 available from Omnova Solutions of Akron, Ohio, FSDS fluorosurfactant diol for solvent systems from PCI Group, Inc. of Phoenix, Ariz., and alkyl alcohols such as Zonyl® BA (1,1,2,2,-tetrahydroperfluoro-1-alkanols ($C_6$-$C_{18}$)), Zonyl® FTS (2-(perfluoroalkyl)ethyl stearate), Zonyl® TBC (triperfluoroalkyl citrate) and Zonyl® BA-L (2-(perfluoroalkyl)ethanol) available from I.E. DuPont de Nemours of Wilmington, Del. In another embodiment, the fluorinated material is a fluorinated hydrocarbon silane. Examples of fluorinated hydrocarbon silanes suitable for use in the contemplated coating include, but are not limited to, nonafluorohexyltrimethoxysilane, nonafluorohexyltriethoxysilane, and (tridecafluoro-1,1,2,2-tetrahydrooctyl)triethoxysilane. In yet another embodiment, the fluorinated material is a fluorinated solvent. Fluorinated solvents also enhance the miscibility of fluorinated hydrocarbon silanes in the coating. Examples of fluorinated solvents suitable for use in the contemplated coating include, but are not limited to, methoxy-nonafluorobutane, 1,1,2,2,3,3,4-heptafluorocyclopentane, perfluorohexane, and 1,1,1,2,3,4,4,5,5,5-decafluropentane. It will be appreciated that the fluorinated materials may also comprise any combination of at least one fluorinated diol, at least one fluorinated hydrocarbon silane, and/or at least one fluorinated solvent. With the addition of the fluorinated material, the thermally-cured coating exhibits a water contact angle of greater than 90° as measured using a goniometer.

In another exemplary embodiment, a method for manufacturing an ophthalmic lens that is abrasion resistant and exhibits hydrophobic properties includes providing a polymeric lens. Any of the polymeric lenses described above may be utilized. Before or after providing the polymeric lens, a coating composition is prepared. The coating composition is prepared by combining at least one liquid polysiloxane and/or at least one polyurethane in a solvent. Any of the above described polysiloxanes and/or polyurethanes can be used. It may be necessary to heat the polysiloxane and/or polyurethane before combining it with the solvent to convert the polysiloxane and/or polyurethane to a liquid state. Any organic solvent may be used to solubilize the polysiloxane and/or polyurethane. Water can also be used at relatively small amounts such as about 5 to about 10 weight percent (wt. %). Suitable organic solvents include mono- and polyalcohols such as ethanol, isopropanol, ethylene glycol, ethylene glycol monobutyl ether, ethylene glycol monophenyl ether, methoxymethoxyethanol, ethylene glycol monoacetate, ethylene glycol diacetate, diethylene glycol, diethylene glycol monomethyl ether, diethylene glycol monobutyl ether, diethylene glycol monobutyl ether acetate, diethylene glycol dimethyl ether, diethylene glycol methylethyl ether, diethylene glycol diethylether, diethylene glycol acetate, triethylglycol, triethylene glycol monomethyl ether, triethylene glycol monoethyl ether, tetraethylene glycol, liquid polyethylene glycols, propylene glycol, propylene glycol monomethyl ether, propylene glycol monoethyl ether, propylene glycolmonobutyl ether, 1-butoxyethoxypropanol, dipropylglycol, dipropylene glycol monomethyl ether, dipropylene glycol ether, tripropylene glycol monomethyl ether, polypropylene glycols, trimethylene glycol, butanedial, 1,5-pentanedial, hexylene glycol, oxylene glycol, oxylene glycol, glycerine, glyceryl acetate, glyceryl diacetate, glyceryl triacetate, trimethylolpropyne, 1,2,6-hexanetrial or derivatives thereof. Hydrophilic ethers (dioxane, trioxane, tetrahydrofuran, tetrahydropyran, methylal), diethylacetal, methyl ethyl ketone, methyl isobutyl ketone, diethyl ketone, acetonylacetone, diacetone alcohol or hydrophilic esters (methyl formate, ethyl formate, propyl formate, methyl acetate, ethyl acetate) may furthermore be used as solvents. The solvent and the polysiloxane and/or the polyurethane are mixed using any suitable mixing or stirring process that forms a mixture. For example, a reflux condenser, a low speed sonicator or a high shear mixing apparatus, such as a homogenizer, a microfluidizer, a cowls blade high shear mixer, an automated media mill, or a ball mill, may be used for several seconds to an hour or more to form the coating base. Alternatively, a commercially available polysiloxane and/or polyurethane in solvent, such as NTPC-e available from Essilor of America, Inc. of Dallas, Tex., can be used. It will be appreciated that, upon mixing with the solvent, the polysiloxane and/or polyurethane may not remain as the polysiloxane or the polyurethane but, rather, may be consumed or transformed to an oligomer derived from the polysiloxane or the polyurethane or a polymer derived from the polysiloxane or the polyurethane.

In an exemplary embodiment, the fluorinated material is added to the polysiloxane and/or polyurethane and solvent combination. It may be necessary to heat the fluorinated material to melting before adding it to the combination. The components are mixed together using any of the above-described methods of mixing until a homogenous coating composition is achieved. It will be appreciated that, while the preferred method of manufacturing the coating composition includes mixing the polysiloxane and/or polyurethane and solvent first, followed by the addition of the fluorinated material, the fluorinated material can be mixed with the solvent first, followed by the addition of the polysiloxane and/or polyurethane. Once the components are combined to form the coating composition, the fluorinated material comprises from about 0.1 to about 10 wt. % of the coating composition comprising the fluorinated materials, the polysiloxane(s), the polyurethane(s), an oligomer derived from the polysiloxane or the polyurethane, and/or a polymer derived from the polysiloxane or the polyurethane, and the solvent(s) (the "total coating composition"), and the polysiloxane(s), the polyurethane(s), an oligomer derived from the polysiloxane or the polyurethane, and/or a polymer derived from the polysiloxane or the polyurethane (the "poly component") and the solvent(s) comprise the remaining 90 wt. % in a ratio of 30:70 poly component:solvent(s).

Upon manufacture of the coating composition, the coating composition is applied overlying the first surface of the polymeric lens and, optionally, overlying the second surface of the polymeric lens. As used herein, the term "overlying" encompasses the terms "on" and "over". Accordingly, the coating composition can be applied directly onto the lens or may be applied over the surface of the lens such that one or more other materials are interposed between the coating composition and the lens. Materials that may be interposed between the coating composition and the lens are those materials that do not hinder the adhesion of the resulting coating to the lens and that do not adversely affect the optical, mechanical, or hydrophobic properties of the resulting coating. In an exemplary embodiment, the coating composition is applied to the lens by dip-coating the lens into the coating composition. In other embodiments, the coating composition is applied to the polymeric lens by painting, spraying, spin coating, rolling, or the like the coating composition overlying the polymeric lens. While it is preferable to apply the coating in a one-step process, such as in one coat, the coating composition can be applied in multiple coatings to achieve a desired thickness. In an exemplary embodiment, once the coating composition is applied to the first surface, and optionally the second surface, of the polymeric lens, the solvents are permitted to evaporate at room temperature (about 16° C. to about 28° C.) or may be heated to the boiling point of the solvents for a sufficient time to permit the solvents to evaporate. Once the solvents have dried to a desired extent, the coating composition is thermally cured at a temperature and time suitable for the polysiloxane(s) and/or polyurethane(s) in the coating composition.

The following are examples of coating compositions and ophthalmic lenses as contemplated herein. The examples are provided for illustration purposes only and are not meant to limit the various embodiments of the present invention in any way.

Example 1

Approximately 0.2 grams of 0.2% nonafluorohexyltrimethoxysilane was combined with 99.8 grams of NTPC-e polysiloxane from Essilor of America and mixed to form a homogenous coating composition. The coating composition contained approximately 30 wt. % solids in an alcohol solvent mixture. A polycarbonate lens was dip-coated in the coating composition and subjected to heat at 90° C. until dried. The lens was then cured at 125° C. for 2 hours. The table below provides testing results comparing a lens with the coating composition and a reference lens with only NTPC-e coated thereon.

|  | NTPC-e Coating | EXAMPLE 1 Coating |
| --- | --- | --- |
| Water contact angle | 82° | 109° |
| Making mark with permanent marker | Clear mark cannot be cleaned with cleaning wipes | Mark barely visible and can be easily wiped off with cleaning wipes |
| Paint spray | Paint sprayed from a 7.62 centimeter (cm) (3 inch) distance; lens surface was completely covered by paint. After 24 hours drying at room temperature, paint cannot be removed with acetone or IPA. | Paint sprayed from a 7.62 cm (3 inch) distance; lens surface had a few paint spots left after spray. After 24 hours drying at room temperature, paint spots removable with acetone or IPA. |

Example 2

Approximately 198 grams of NTPC-e was combined with 2 grams of 1% PolyFox 6520 fluorosurfactant diol and 1.92 grams of 3M HFE 7100 methoxy-nonafluorobutane to form a homogeneous coating composition. The PolyFox and 3M HFE 7100 were present in the coating composition in a 4:96 ratio by weight. The coating composition was applied on 30 76-millimeter (mm) bisphenol A polycarbonate lenses by dip-coating. The lenses were subjected to heat at 90° C. for 10 minutes until dry. The lenses were then cured at 125° C. for 2 hours resulting in a coating thickness of 5 microns (μm). The following tests were performed.

Test 1: Bayer Abrasion Test (Oscillating Sand)

Three coated lenses were tested using the Bayer Abrasion Test (Oscillating Sand) according to Colts SOP #11-10-08 and using a Colts BTE Bayer tester. 500-gram portions of Kryptonite B were used as the abrasive media. The lenses were mounted on the bottom of approximately 25 cm by 25 cm pans along with an uncoated CR-39 cast resin reference lens. The 500 gram portion of mineral abrasive was placed on the bottom of the pan and the pan was oscillated for 600 cycles (1200 strokes) dragging the abrasive media across the test and reference lenses. Haze, the amount of forward scattered light that deviates from the incident light by more than 2.5°, was measured before and after abrasion of the lens. The increase in haze following abrasion (haze gain or delta haze) was calculated for the test and reference lenses. The results were reported as the Bayer Ratio:

Bayer Ratio=$\Delta Haze_{Ref}/\Delta Haze_{Test}$

The Bayer Ratio was 3-4 for the coated lenses indicating high abrasion resistance.

Test 2: Marker Test

Marks were made on 3 coated lenses with a Sharpie® Marker available from Newell Rubbermaid Office Products of Oakbrook, Ill. The marks were easily removed from the coated lenses with a paper tissue. A reference lens coated only with NTPC-e was subjected to the same testing procedure. The marks were not removable with paper tissue.

Test 3: Durability Test via Modified Steel Wool Tester

A Colts STE steel wool tester was modified with cotton cloth. Marks were made on 3 coated lenses with a Sharpie® Marker available from Newell Rubbermaid Office Products of Oakbrook, Ill. The durability of the easy clean feature of the coating was evaluated by wiping the coated lenses with the cotton cloth 200 times (200 cycles at 60 cycles per minutes). Marks were made at 50, 100, 150, and 200 intervals. After 200 cycles, marks were easily removed with a paper tissue. A reference lens coated only with NTPC-e was subjected to the same testing procedure. The marks were not removable from the reference lens with paper tissue.

Test 4: Durability Test in Artificial Perspiration

Three coated lenses were soaked in Artificial Eccrine Perspiration-stabilized available from Pickering Laboratories, Inc. of Mountain View, Calif., for 18 hours. After soaking, the lenses were wiped dry and marks were made on the lenses using a Sharpie® Marker. The marks were easily removed with a paper tissue. A reference lens coated only with NTPC-e was subjected to the same testing procedure. The marks were not removable with paper tissue.

Test 5: Durability Test in Deionized Water

Three coated lenses were soaked in deionized water for 18 hours. After soaking, the lenses were wiped dry and marks were made on the lenses using a Sharpie® Marker. The marks were easily removed with a paper tissue. A reference lens coated only with NTPC-e was subjected to the same testing procedure. The marks were not removable with paper tissue.

Test 6: Contact Angle Measurement

The water contact angle on a coated lens was measured at 109° by a goniometer.

Test 7: Paint Spray Test

A coated lenses was sprayed with Krylon® semi-gloss white spray paint available from Krylon, Inc. of Norristown, Pa. from a 7.62 cm (3 inch) distance. The coated lens had a few paint spots on its surface after spraying. The paint spots were permitted to dry for 24 hours at room temperature. After 24 hours, the paint spots were removable by acetone and isopropyl alcohol.

Accordingly, coating compositions, ophthalmic lenses comprising coatings, and methods for manufacturing ophthalmic lenses having the coatings have been described. The coating compositions include a thermally-curable polysiloxane(s) or polyurethane(s), or a combination thereof and fluorinated material incorporated therein. Compared to conventional coating compositions, the coating compositions contemplated herein can be applied in a single application and thermally cured, thus decreasing the cost and time of manufacturing and increasing production. In addition, the thermally-curable coating imparts scratch and abrasion resistance to the ophthalmic lenses. Further, the fluorinated material causes the thermally-cured coatings to exhibit hydrophobic surface properties without altering the curing properties or the optical or mechanical performance of the polysiloxane and/or polyurethane components. Thus, the resulting ophthalmic lenses are resistant to abrasion, scratching, stains, and markings and can easily be cleaned by wiping with a clean cloth, tissue paper, or the like.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A coating composition for an ophthalmic polymeric lens, the coating composition comprising:
    a poly component, wherein the poly component comprises a polysiloxane, a polyurethane, an oligomer derived from a polysiloxane or a polyurethane, a polymer derived from a polysiloxane or a polyurethane, or a combination thereof;
    a solvent; and
    a fluorinated material,
wherein a thermally cured coating resulting from the coating composition exhibits a water contact angle of greater than 90° as measured by a goniometer when applied in a single coat on the ophthalmic polymeric lens, wherein the poly component and the solvent are present in an amount of from about 90 to about 99.9 wt. % of a total composition comprising the poly component, the solvent, and the fluorinated material, in a ratio of 30:70 poly component:solvent and wherein the fluorinated material comprises a fluorinated surfactant selected from the group consisting of 1,1,2,2-tetrahydroperfluoro-1-alkanols of chain length $C_6$-$C_{18}$, 2-(perfluoroalkyl)ethyl stearate, tripefluoroalkyl citrate, 2-(perfluoroalkyl)ethanol and/or mixtures thereof.

2. The coating composition of claim 1, wherein the polysiloxane comprises a material selected from the group consisting of polysiloxanes having amino functional groups, polysiloxanes having epoxy functional groups, linear siloxanes, and cyclic siloxanes.

3. The coating composition of claim 1, wherein the fluorinated material is present in the total composition in an amount of from about 0.1 to about 10 wt. % of the total composition.

* * * * *